United States Patent [19]

Ueno

[11] Patent Number: 5,300,062

[45] Date of Patent: Apr. 5, 1994

[54] PHOTOCOAGULATOR

[75] Inventor: Tokio Ueno, Gamagori, Japan

[73] Assignee: Hidek Co., Ltd., Aichi, Japan

[21] Appl. No.: 791,692

[22] Filed: Nov. 14, 1991

[30] Foreign Application Priority Data

Nov. 16, 1990 [JP]   Japan .................................. 2-312006

[51] Int. Cl.⁵ .............................................. A61B 17/32
[52] U.S. Cl. ............................................. 606/4; 606/17; 606/16
[58] Field of Search ...................... 606/2, 3, 4, 16, 17, 606/18; 128/395, 397, 398; 604/101

[56]  References Cited

U.S. PATENT DOCUMENTS

| | | | |
|---|---|---|---|
| 3,622,743 | 11/1971 | Muncheryan | 606/2 |
| 4,445,892 | 5/1984 | Hussein et al. | 606/18 |
| 4,580,557 | 4/1986 | Hertzmann | 128/395 |
| 4,719,912 | 1/1988 | Weinberg | 606/4 |
| 4,732,460 | 3/1988 | Kele et al. | 606/4 |
| 5,147,349 | 9/1992 | Johnson et al. | 606/15 |

FOREIGN PATENT DOCUMENTS 0335714  10/1989  European Pat. Off. ................ 606/6

*Primary Examiner*—Stephen C. Pellegrino
*Assistant Examiner*—Sonya C. Harris
*Attorney, Agent, or Firm*—Nikaido, Marmelstein, Murray & Oram

[57]  ABSTRACT

A photocoagulator for guiding a semiconductor laser beam to an eye to be treated for a photocoagulation operation. The photocoagulator comprises a main device for incorporating first semiconductor laser light sources, an auxiliary device for incorporating second semiconductor laser light sources, an optical fiber for guiding to the auxiliary device output beams from the first semiconductor laser light sources incorporated in the main device, a combining optical element disposed in the auxiliary device for combining the output beams from the first semiconductor laser light sources and the output beams from the second semiconductor laser light sources into a combination beam, and a beam guide optical system for guiding the combination beam combined by the combining optical element to the eye to be treated. The photocoagulator having such an arrangement is made compact and can emit a laser beam having a sufficient energy level.

19 Claims, 3 Drawing Sheets

FIG. I
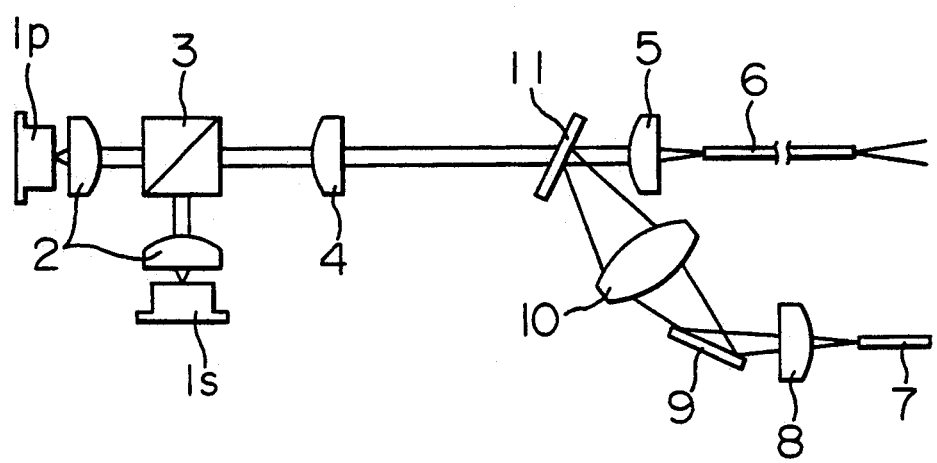
FIG. 2
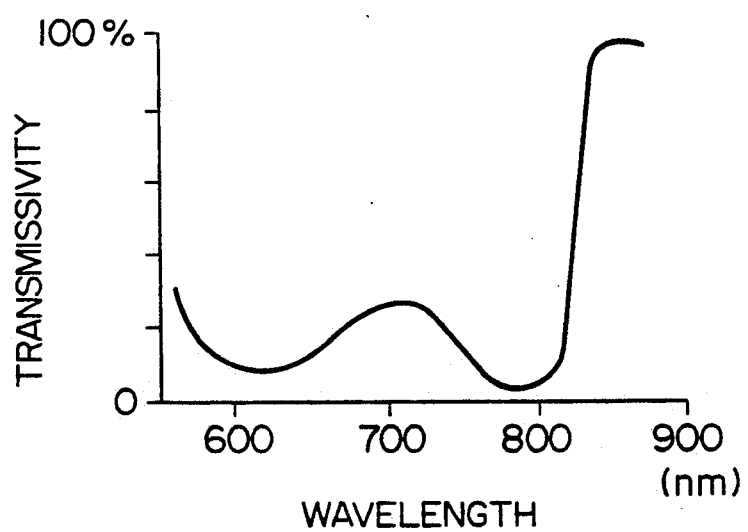

PHOTOCOAGULATOR

FIELD OF THE INVENTION

The present invention generally relates to photocoagulators and, more particularly, to a photocoagulator which utilizes a laser beam to treat a patient's eye and which is suitable, in particular, for such a treatment as to require a high output laser beam.

BACKGROUND OF THE INVENTION

Prior art photocoagulators generally have used such an ion laser as an argon laser but have been defective in that the photocoangulators are large in size and have employed a water cooling system.

In order to overcome such defects, there has been proposed an attempt to use a semiconductor laser which is small in size and based on an air cooling system. However, such an existing semiconductor laser can have an output as low as at most about 1.5 W. In addition, since the laser beam emitted from the optical fiber spreads more widely than an ion laser beam or the like, the semiconductor laser cannot produce a sufficient output power. For the purpose of increasing the quantity or power of laser beam to be directed to the input end of the optical fiber for laser beam to obtain a sufficient output power, there has been proposed such a method that two light sources of semiconductor are provided to combine laser beams emitted from the respective light sources with use of a polarizer or the like.

As the clinical application of the photocoagulator using the semiconductor laser is recently increased, transscleral cyclophotocoagulation by a semiconductor laser has been attempted for the purpose of reducing the intraocular pressure in glaucoma treatments.

However, even when the prior art photocoagulator using two laser light sources is employed, the photocoagulator has not been able to produce an output power as high as effective for the transscleral cyclophotocoagulation, because the resultant laser beam, i.e., the output power from the optical fiber of the photocoagulator is as low as at most about 2 W.

Theoretically, the output of the photocoagulator can be increased as the number of laser light sources built in the photocoagulator is increased. In actual applications, however, since the photocoagulator is complicated in laser beam combination manner and also poor in beam combination efficiency, such a photocoagulator that can be made compact and can produce an effective output power has not existed so far.

SUMMARY OF THE INVENTION

It is therefore an object of the present invention to provide a photocoagulator which can have a feature that a photocoagulator using a semiconductor laser or lasers can be made small in size and which can produce an effective output power.

In accordance with the present invention, the above object is attained by providing a photocoagulator which comprises a main device for incorporating first semiconductor laser light sources, an auxiliary device for incorporating second semiconductor laser light sources, an optical fiber for guiding to the auxiliary device output beams of the first semiconductor laser light sources incorporated in the main device, a combining optical element disposed in the auxiliary device for combining the output beams from the first semiconductor laser light sources and the output beams from the second semiconductor laser light sources into a combination beam, and a beam guide optical system for guiding the combination beam combined by the combining optical element to the eye to be treated.

In the present invention, a laser beam from the first semiconductor laser light sources incorporated in the main device as well as a laser beam from the second semiconductor laser light sources incorporated in the auxiliary device are synchronously irradiated onto an eye to be treated. As a result, the photocoagulator can produce a high power output and thus transscleral cyclophotocoagulation or the like can be easily realized.

BRIEF DESCRIPTION OF THE DRAWINGS

FIG. 1 shows an arrangement of an optical system used in an auxiliary device;

FIG. 2 shows a characteristic of a dichroic mirror; and

DESCRIPTION OF THE PREFERRED EMBODIMENTS

Figure 3:
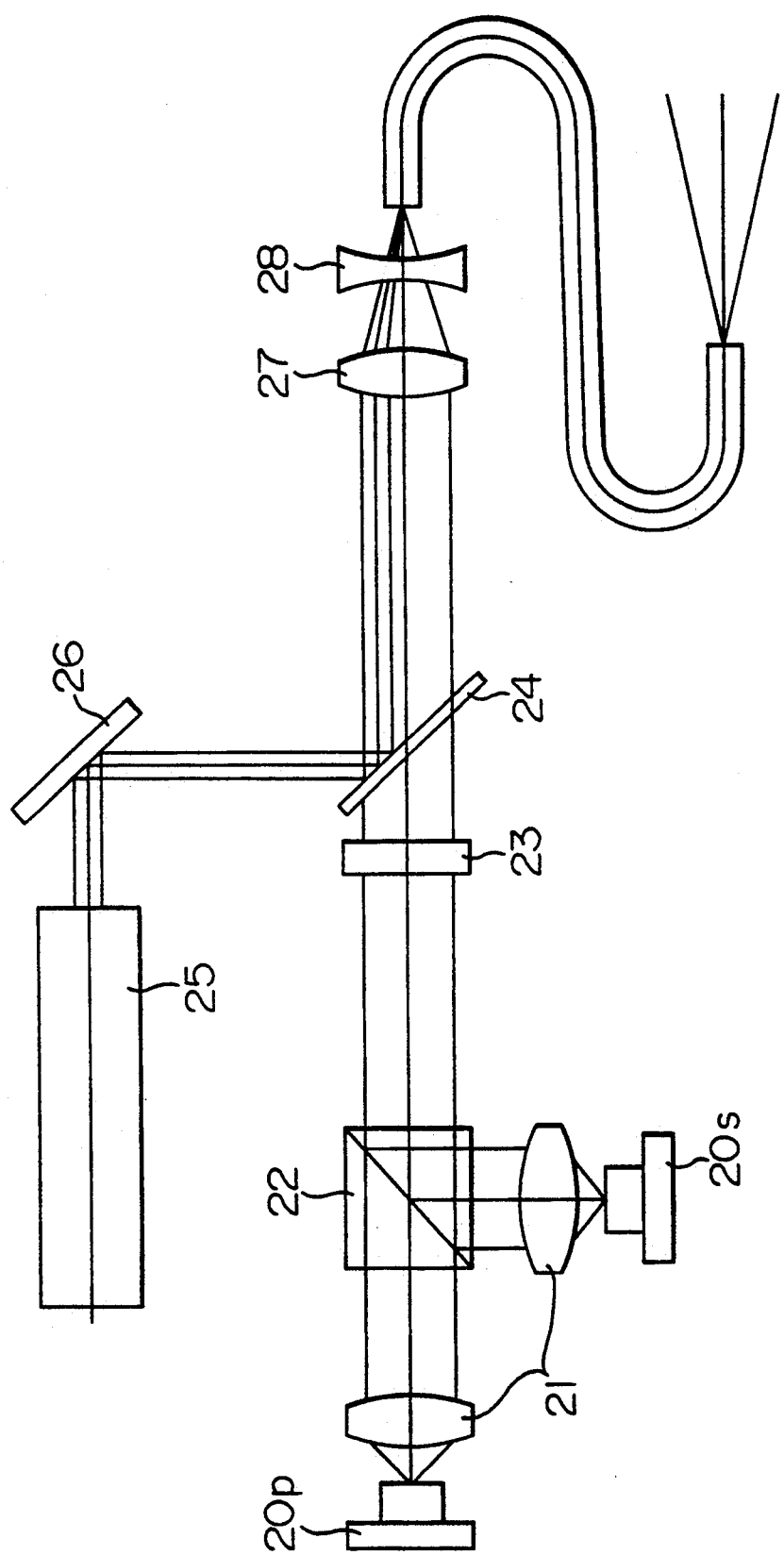
FIG. 3 shows an arrangement of an optical system used in a main device.

An embodiment of the present invention will be explained in the following with reference to the accompanying drawings.

Referring first to FIG. 1, there is shown an arrangement of an optical system used in an auxiliary device. In the drawing, reference symbols 1p and 1s denote sub semiconductor laser light sources for treatment which, in the present embodiment, each emit a laser beam having a wavelength $\lambda$ of 845 nm. Reference numeral 2 denotes a collimater lens through which the astigmatic laser beam emitted by the laser light sources 1p and 1s are converted into parallel beams in their one directions. Reference numeral 3 denotes a polarizing beam coupler which combines the laser beams output by the two semiconductor laser light sources 1p and 1s into a single beam. The polarizing beam coupler 3 has such a property that transmits P polarized beam therethrough but reflects S polarized beam with respect to a wavelength $\lambda = 845$ nm and the P polarized beam is emitted from the laser right source 1p while the S polarized beam is from the other laser right source 1s. Accordingly, the polarizing beam coupler 3 can combine the two sub laser beams for treatment into a single beam without loss.

Reference numeral 4 represents a condenser lens and numeral 5 represents a cylindrical condenser lens. The condenser lens 4 and the cylindrical condenser lens 5 cooperatively act to focus the laser beam combined through the polarizing beam coupler 3 and to direct it efficiently to an optical fiber 6 which guides the incident beam to an eye to be treated. Transscleral cyclophotocoagulation can be carried out, for example, by connecting the other end of the optical fiber 6 to a contact probe having a sapphire chip, but may also be carried out by replacing the contact probe by an end photoprobe or the like.

Reference numeral 7 denotes another optical fiber which can be connected to the main device through a connector and which transmits a main semiconductor laser beam for treatment (having a wavelength $\lambda$ of 810 nm in the present embodiment) and a guide beam (He-Ne laser beam having a wavelength λ of 632.8 nm in the present embodiment) from the main device. Reference numeral 8 denotes a cylindrical projection lens and numeral 9 denotes a mirror for changing the direction of the beam. The cylindrical projection lens 8 is disposed because the cylindrical condenser lens 5 is provided in an optical path. Numeral 10 denotes a projection lens which acts to project the end face of the optical fiber 7 onto the end face of the optical fiber 6 in cooperation with the cylindrical projection lens 8 and the cylindrical condenser lens 5, whereby the main semiconductor laser beam for treatment and the guide beam are directed to the optical fiber 6.

Numeral 11 denotes a dichroic mirror which combines the main semiconductor laser beam, guide beam and sub semiconductor laser beam into a single beam and which is disposed so as to have an incident angle of 20 degrees, to the three types of laser beams.

In this case, the incident angle is set to be small. This is because the polarization directions of the sub semiconductor laser beams from the light sources 1p and 1s correspond to P and S components with respect to the dichroic mirror 11 respectively and when the incident angle is set to be large, the transmission characteristics of the P and S components are largely shifted, thus resulting in that the two sub laser beams become different in transmissibility from each other. In the actual optical design, it is desirable to set the incident angle as small as possible.

The dichroic mirror 11 has such a characteristic as shown in FIG. 2, that is, the mirror reflects incident light having wavelengths λ of 810 nm and 632.8 nm and transmits incident light having a wavelength λ of 845 nm when the incident angle is set at 20 degrees.

The dichroic mirror having the characteristic of FIG. 2 is made in the form of an infrared-ray separating filter comprising a glass substrate having a refractive index of 1.5 and 25 layers alternately coated on the substrate with a titanium oxide ($TiO_2$) layer and a silicon dioxide ($SiO_2$) layer. It is necessary to suitably select the characteristic of the dichroic mirror 11 taking into consideration the wavelengths and incident angles of the main, sub semiconductor laser beam for treatment, and the guide beam to be used.

The main semiconductor laser beam for treatment and guide beam are reflected by the dichroic mirror 11 and the sub semiconductor laser beam is transmitted through the mirror 11 so that both of main, sub laser beam for treatment, and the guide beam can be combined into a single beam.

Figure 4:
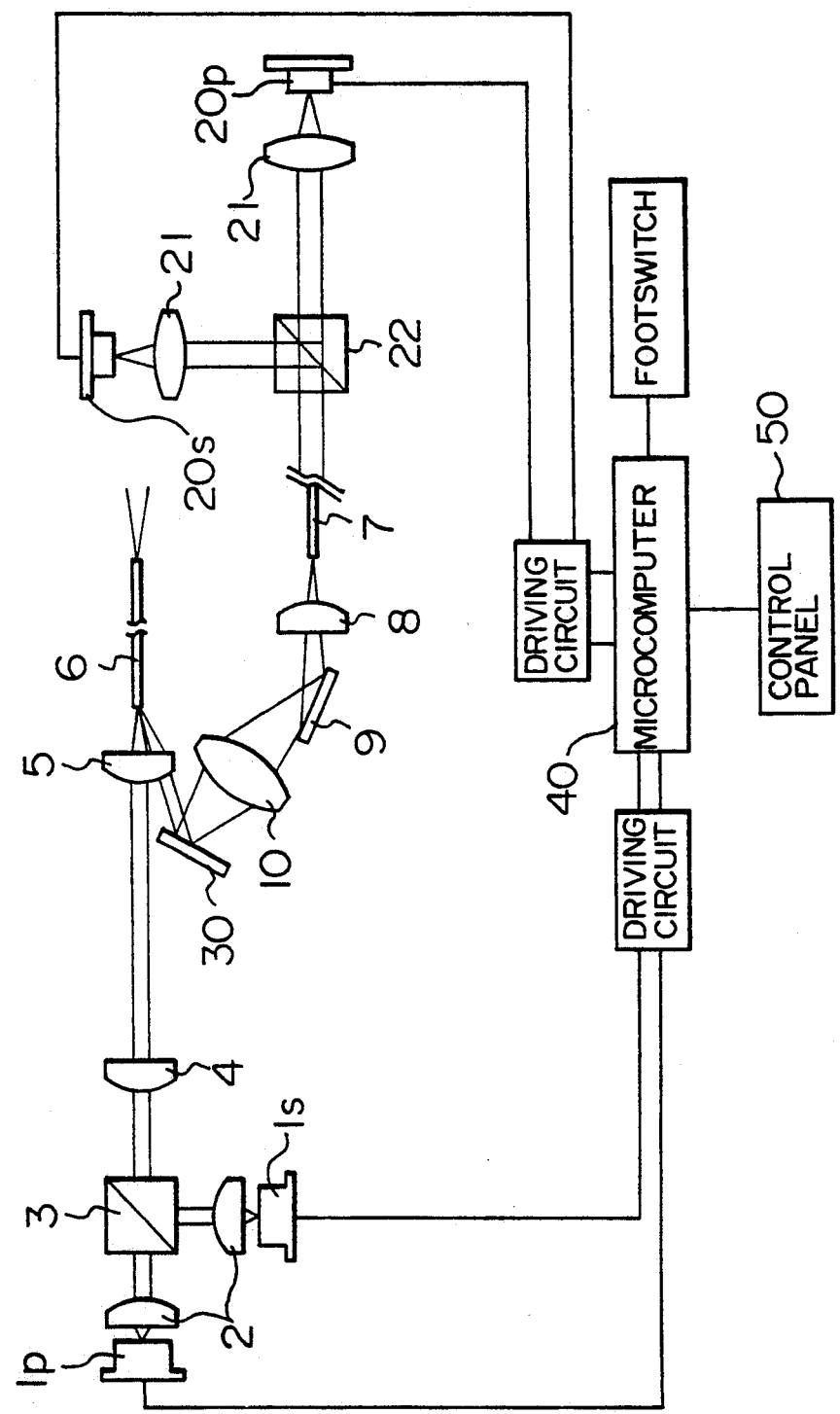
FIG. 4 shows an arrangement of optical system of an embodiment in which a mirror is disposed out of the axis of the optical path.

When the main and sub semiconductor laser beams for treatment have the same wavelength, the dichroic mirror 11 is replaced by a mirror 30 arranged out of the axis of the optical path. Refer to FIG. 4)

Explanation will next be made as to the optical system of the main device by referring to FIG. 3.

Reference symbols 20p and 20s denote main semiconductor laser light sources for treatment each of which emits a laser beam having a wavelength λ of 810 nm in the present embodiment. Like the sub semiconductor laser beams for treatment, the astigmatic main laser beams emitted are converted into two parallel beams directed in their one directions by means of respective collimater lenses 21, respectively. The two collimated main laser beams are then combined at a polarizing beam coupler 22 into a single beam. In the present embodiment, a cylindrical lens 23 is additionally provided to correct the astigmatism of the laser beam.

Numeral 24 denotes a dichroic mirror which has such a characteristic that transmits the main semiconductor laser beam for treatment therethrough but reflects a He-Ne laser beam.

Reference numeral 25 denotes a He-Ne laser light source and numeral 26 denotes a mirror. The main semiconductor laser beam and the He-Ne laser beam are combined at the dichroic mirror 24 into a single beam, in which case the He-Ne laser beam is directed as biased in optical axis with respect to the main semiconductor laser beam, whereby the divergence angle of an He-Ne laser beam output by the optical fiber 7 can coincide with that of the main semiconductor laser beam.

Reference numerals 27 and 28 denote condenser lenses which cooperatively focus the combined laser beam on one end of the optical fiber 7.

As already explained above/the optical fiber 7 is attached at its free end with a male connector and the main device is attached with a female connector so that the both connectors can be detachably connected. The type of the connector is not limited in particular but one-step coupling type based on a click mechanism is desirable. Since the optical fiber 7 is detachably connected to the main device in this way, various sorts of photocoagulations can be realized by plugging the male connector leading to a slit lamp, a binocular indirect ophthalmoscope, etc. into the female connector on the side of the main device. Even when a detachable connector is attached to the end of the optical fiber 7 on the side of the auxiliary device, the similar effect can be realized.

The sub semiconductor laser light sources 1p and 1s can oscillate in synchronism with or independently of the main semiconductor laser light sources 20p and 20s under the control of a microcomputer 40 (Refer to FIG. 4) provided in the main device (which may be provided in the auxiliary device but not reasonable). These selections are performed by operating the switches of the control panel 50 attached with the main device.

Similarly, the outputs of the main semiconductor laser light sources 20p and 20s may be changed in synchronism with or independently of the outputs of the sub semiconductor laser light sources 1p and 1s to realize a desired treatment beam.

Explanation will then be directed to the operation of the embodiment with the optical systems having such arrangements as mentioned above, in connection with the case where the main semiconductor laser light sources 20p and 20s as well as the sub semiconductor laser light sources 1p and 1s oscillate synchronously as an example.

An operator operates switches provided on a control panel 50 of the main device to select a synchronous mode, adjust output beams and then oscillate the He-Ne laser light source 25 of the guide beam. This causes the oscillated guide beam to be reflected by the dichroic mirror 24 and then be focused by the condenser lenses 27 and 28 on the optical fiber 7 connected to the main device through the connector.

On the other hand, in the auxiliary device, the guide beam emitted from the optical fiber 7 is reflected by the mirror 9 and the dichroic mirror 11 or mirror 30 and made incident upon one end of the optical fiber 6 through a group of fiber end projection lenses (cylindrical projection lens 8, projection lens 10 and cylindrical condenser lens 5). The guide beam directed to the optical fiber 6 is passed through the fiber, emitted from the output end of the end photoprobe and then irradiated on a spot to be treated.

After the operator sets a suitable distance between the output end of the fiber 6 and the spot to be treated and determines its irradiation range, as discussed above, the operator starts the oscillation of the main semiconductor laser light sources 20p and 20s. The main semiconductor laser beams are combined by the polarizing beam coupler 22, passed through the dichroic mirror 24, passed through the same optical path as the guide beam and then directed to the optical fiber 6.

At the same time that the main laser light sources 20p and 20s oscillate, the oscillation of the sub laser light sources 1p and 1s is started under the control of the microcomputer 40. The oscillated sub semiconductor laser beams are collimated through the associated collimator lenses 2, combined by the polarizing beam coupler 3, further combined by the dichroic mirror 11 (or by the mirror 30) with the main semiconductor laser beam, and then directed to the input end of the optical fiber 6 through the focusing cylindrical condenser lens 5.

The main and sub semiconductor laser beams for treatment incident on the optical fiber 6 are passed through the fiber 6, emitted from the output end of the fiber 6 and then irradiated onto a spot to be treated.

After completing the treatment, the operator stops the emission of the main semiconductor laser beam, at which time the oscillation of the sub semiconductor laser light sources 1p and 1s is automatically stopped under the control of the microcomputer 40 at the same time.

In accordance with the present invention, since the semiconductor lasers can produce a sufficient output power, such photocoagulation as has been so far impossible, due to an insufficient output power in the prior art, can be realized.

Further, since the operator can connect the main semiconductor laser beam for treatment and the guide beam to the auxiliary device as necessary, the operator can conduct various treatments through very simple operations and in various ways.

In addition, since the main semiconductor laser beam is different in wavelength from the sub semiconductor laser beam, the wavelength effective for the treatment can be selectively used and thus treatment effect can be enhanced.

Although the present invention has been described in detail, it should be understood that various changes, substitutions and alternation can be made hereto without departing from the spirit and scope of the present invention as defined by the appended claims.

What is claimed is:

1. A photocoagulator for guiding a semiconductor laser beam to an eye to be treated for a photocoagulation operation, comprising:
   a main layer unit comprising a first plurality of semiconductor laser light sources producing output beams;
   an auxiliary laser unit separate from said main laser unit comprising at least one second semiconductor laser light source producing an output beam;
   an optical fiber detachably provided between said main laser unit and said auxiliary laser unit, said optical fiber guiding said output beams from said first plurality of semiconductor laser light sources of said main laser unit to said auxiliary laser unit;
   a combining optical means, disposed in said auxiliary laser unit, for combining a) the output beams, guided by said optical fiber from said first plurality of semiconductor laser light sources, and b) the output beam from said at least one second semiconductor laser light source into a combination beam; and
   a beam guide optical means for guiding said combination beam combined by said combining optical means to said eye to be treated.

2. A photocoagulator as set forth in claim 1, wherein said first plurality of semiconductor laser light sources have means producing said output beams having one wavelength and said at least one second semiconductor laser light source has means producing said output beam having an identical wavelength to said one wavelength.

3. A photocoagulator as set forth in claim 2, further comprising a selecting means for selecting one of the beam emissions of said first plurality of semiconductor laser light sources and the beam emission of said at least one second semiconductor laser light source.

4. A photocoagulator as set forth in claim 1, wherein said first plurality of semiconductor laser light sources have means producing said output beams having one wavelength and said at least one second semiconductor laser light source has means producing said output beam having a different wavelength to said one wavelength.

5. A photocoagulator as set forth in claim 4, wherein said combining optical means is a dichroic mirror.

6. A photocoagulator as set forth in claim 4, further comprising synchronization means for controlling beam emission of said at least one second semiconductor laser light source in synchronism with beam emission of said first plurality of semiconductor laser light sources.

7. A photocoagulator as set forth in claim 6, further comprising adjustment means for adjusting said output beams of said first plurality of semiconductor laser light sources independently of said output beam of said at least one second semiconductor laser light source.

8. A photocoagulator as set forth in claim 2, further comprising synchronization means for controlling beam emission of said at least one second semiconductor laser light source in synchronism with beam emission of said first plurality of semiconductor laser light sources.

9. A photocoagulator as set forth in claim 8, further comprising adjustment means for adjusting said output beams of said first plurality of semiconductor laser light sources independently of said output beam of said at least one second semiconductor laser light source.

10. A photocoagulator as set forth in claim 8, further comprising selecting means for selecting one of the beam emissions of said first plurality of semiconductor laser light sources and the beam emission of said at least one second semiconductor laser light source.

11. A photocoagulator as set forth in claim 1, wherein said auxiliary laser unit further comprises plural second semiconductor laser light sources, a plurality of collimator lenses for converting respective beams emitted by each of said second semiconductor laser light sources into parallel beams, and a polarizing beam coupler means for combining said beams emitted by each of said second semiconductor laser light sources into a single beam.

12. A photocoagulator as set forth in claim 1, wherein said combining optical means comprises a dichroic mirror, said dichroic mirror being in the form of an infrared-ray separating filter comprising a glass substrate having a refractive index of approximately 1.5 and a plurality of alternating titanium oxide layers and silicon dioxide layers.

13. A photocoagulator as set forth in claim 1, wherein said first plurality of semiconductor laser light sources in said main laser unit comprises a plurality of treatment laser light sources and a He-Ne laser light source.

14. A photocoagulator as set forth in claim 13, wherein said main laser unit further comprises collimator lenses for converting respective beams emitted by each of said plurality of treatment laser light sources into parallel beams, and a polarizing beam coupler means for combining said beams emitted by each of said plurality of treatment laser light sources into a single beam.

15. A method for generating a laser beam having a high energy level, comprising the steps of:
   combining, in a main laser unit, first and second laser beams emitted from first and second semiconductor elements having mutually different polarizations into a third laser beam by means of a first polarizing beam coupler;
   combining, in an auxiliary laser unit, fourth and fifth laser beams emitted from third and fourth semiconductor elements having mutually different polarizations into a sixth laser beam by means of a second polarizing beam coupler;
   detachably providing an optical fiber between said main laser unit and said auxiliary laser unit; and
   combining said third and sixth laser beams by means of a dichroic mirror.

16. A method of claim 15, wherein said third and sixth laser beams have identical wavelengths.

17. A method of claim 15, wherein said third and sixth laser beams have different wavelengths.

18. A method of claim 15, further comprising operating said first and second semiconductor elements synchronously with said third and fourth semiconductor elements.

19. A photocoagulator for guiding a semiconductor laser beam to an eye to be treated for a photocoagulation operation, comprising:
   a main laser unit comprising a first plurality of semiconductor laser light sources producing output beams, said output beams include a guide beam and an output treatment beam;
   an auxiliary laser unit separate from said main laser unit comprising at least one second semiconductor laser light source producing an output treatment beam;
   an optical fiber means, provided between said main laser unit and auxiliary laser unit, for guiding said output beams from said first plurality of semiconductor laser light sources of said main laser unit to said auxiliary laser unit;
   a combining optical means, disposed in said auxiliary laser unit, for combining the output beams from said first plurality of semiconductor laser light sources and the output beam from said at least one second semiconductor laser light source into a combination beam; and
   a beam guide optical means for guiding said combination beam combined by said combining optical means to said eye to be treated.

* * * * *

UNITED STATES PATENT AND TRADEMARK OFFICE
CERTIFICATE OF CORRECTION

PATENT NO. : 5,300,062
DATED : April 5, 1994
INVENTOR(S) : Tokio Ueno

It is certified that error appears in the above-indentified patent and that said Letters Patent is hereby corrected as shown below:

On the title page, Item [73], change "Hidek" to --Nidek--.

Signed and Sealed this

Sixteenth Day of August, 1994

BRUCE LEHMAN

*Attest:*

*Attesting Officer*  *Commissioner of Patents and Trademarks*